United States Patent [19]

Tordeux et al.

[11] Patent Number: 4,794,200

[45] Date of Patent: Dec. 27, 1988

[54] PROCESS FOR THE PREPARATION OF TRIFLUOROMETHYL IODIDE

[75] Inventors: Marc Tordeux, Sceaux; Claude Wakselman, Paris, both of France

[73] Assignee: Rhone-Poulenc Chimie, France

[21] Appl. No.: 106,347

[22] Filed: Oct. 9, 1987

[30] Foreign Application Priority Data

Oct. 10, 1986 [FR]  France ................................ 86 14283

[51] Int. Cl.⁴ ...................... C07C 17/20; C07C 19/07
[52] U.S. Cl. .................................................. 570/170
[58] Field of Search ........................................ 570/170

[56] References Cited

U.S. PATENT DOCUMENTS 2,531,372  11/1950  Waterman et al. ................... 570/170
4,221,734   9/1980  Commeyras et al. ............... 260/408
4,222,967   9/1980  Boehm et al. ........................ 570/170

FOREIGN PATENT DOCUMENTS 165135  12/1985  European Pat. Off. .
0184896  6/1986  European Pat. Off. ............ 570/170
48286  12/1974  Japan ................................... 570/170

OTHER PUBLICATIONS

Howells et al., "Trifluoromethanesulfonic Acid and Derivatives," Chemical Reviews, vol. 77, p. 69, (1977).
Blancou et al., "Preparation of Perfluoroalkane Carboxylic and Sulphonic Acid Derivatives by the Action of Metallic Couples of Perfluoroalkyl Iodides in Dimethyl Sulphoxide," J.C.S. Chem. Comm. pp. 885–886.
Krespan, "Preparation of Fluoroalkyl Iodides from Fluorinated Acid Chlorides," Journal of Organic Chemisstry, vol. 23, p. 2016 (1958).
Paskovich et al., "Simplified Method for the Preparation of Fluoroalkyl Iodides," Journal of Organic Chemistry, vol. 32, p. 833 (1967).
Haszeldine, "The Reactions of Metallic Salts of Acids with Halogens. Part I. The Reaction of Metal Trifluoroacetates with Iodine, Bromine, and Chlorine," Journal of the Chemical Society, No. 124, p. 584 (191).
Banks et al., "The Reaction of Bromine Trifluoride and Iodine Pentafluoride with Carbon Tetrachloride, Tetrabromide, and Tetraiodide and with Tetraiodoethylene," Journal of the Chemical Society, No.443, p. 2188 (1948).

Primary Examiner—J. E. Evans
Attorney, Agent, or Firm—Finnegan, Henderson, Farabow, Garrett, & Dunner

[57] ABSTRACT

A process for the preparation of trifluoromethyl iodide by bringing into contact with one another to form a reaction product either:
zinc, sulfur dioxide, and trifluoromethyl bromide, or
(b) sodium dithionite and trifluoromethyl bromide;
in a polar aprotic solvent, such as dimethylformamide, preferably followed by a filtration stage to remove the solid products. Thereafter, iodine dissolved in carboxylic or sulfuric acid is added to the reaction product, and trifluoromethyl iodide is evolved.

18 Claims, No Drawings

PROCESS FOR THE PREPARATION OF TRIFLUOROMETHYL IODIDE

The present invention relates to a process for the preparation of trifluoromethyl iodide. More particularly, it relates to a process for the conversion of trifluoromethyl bromide into trifluoromethyl iodide.

Trifluoromethyl iodide is currently an extremely expensive product whereas its brominated analog trifluoromethyl bromide is inexpensive.

There are at least four processes described in the art for the preparation of trifluoromethyl iodide.

The first, described by BANKS, EMELEUS, HASZELDINE and KERRIGAN in the Journal of the Chemical Society, p. 2188 (1948), consists of reacting carbon tetraiodide with iodine pentafluoride for thirty minutes at 90°–100° C. This process cannot be used on an industrial scale because carbon tetraiodide is not commercially available.

The second process for the preparation of trifluoromethyl iodide, described by HASZELDINE in the Journal of the Chemical Society, p. 584 (1951), consists of reacting silver trifluoroacetate with iodine. The yields reported are very high (91%), but the high cost and the toxicity of silver trifluoroacetate prevent this process from being used at the industrial level.

The third process for the preparation of $CF_3I$, described by KRESPAN in the Journal of Organic Chemistry 23 (1958) page 2016, consists of reacting trifluoroacetyl chloride with potassium iodide at 200° C. for 6 hours, with an overall reaction yield not exceeding 30%. Trifluoroacetyl chloride is an expensive gas and the yields are poor, which makes this process too expensive for use on an industrial scale.

The fourth process for the preparation of $CF_3I$, described by PASKOVICH, GASPAR and HAMMOND in the Journal of Organic Chemistry 32 (1967) page 833, consists of reacting sodium trifluoroacetate with iodine suspended in refluxed dimethylformamide at a temperature of approximately 140° C. However, on an industrial scale, the use of dimethylformamide under reflux, in the presence of iodine and in an aprotic medium, presents safety problems.

The disadvantages of these prior art processes for synthesizing trifluoromethyl iodide, considered together, explain the extremely high cost of this chemical.

Because $CF_3I$ has many applications, the chemicals industry has heretofore sought an inexpensive process for the preparation of $CF_3I$. Perfluoroalkyl iodides are reagents which are very useful for the preparation of polyfluorinated alcohols or carboxylic and sulfonic acids.

Perfluoroalkyl iodides, the alkyl chain of which contains an even number of carbon atoms, are produced at a low price on an industrial scale starting with tetrafluoroethylene, which is commonly available, as the starting material. In contrast, trifluoromethyl iodide, is produced in only very small quantities by techniques which are very difficult, as described above.

The subject of the present invention is a safe and economically viable process for the preparation of trifluoromethyl iodide starting with trifluoromethyl bromide, a gas readily available on the chemicals market since it is employed as an extinguishing gas in electronics.

More particularly, the subject of the present invention is a process for the preparation of $CF_3I$ which comprises, in a first stage, introducing into a polar solvent, either a metal selected from the group consisting of zinc, cadmium, aluminum and manganese, together with sulfur dioxide, or an alkali metal dithionite. This is followed by the addition of trifluoromethyl bromide at a pressure greater than one bar for a time sufficient to react.

The method of introducing into a polar solvent a metal selected from the group consisting of zinc, cadmium, aluminum, and manganese, together with sulfur dioxide, followed by addition of trifluoromethyl bromide, is the subject of copending application Ser. No. 06/931,984, filed Nov. 24, 1986, which application is incorporated specifically by reference herein.

The method of introducing into a polar solvent an alkali dithionite, followed by addition of trifluoromethyl bromide, is the subject of copending application Ser. No. 07/011,884, filed Feb. 6, 1987, which application is incorporated specifically by reference herein.

After the first stage, a second stage, preferably following filtration, comprises adding iodine and a carboxylic or sulfonic acid, which acid may be perfluorinated to the reaction product of the first stage for a time sufficient to form $CF_3I$.

The process of the present invention does not employ any expensive or dangerous starting materials and enables trifluoromethyl iodide to be obtained easily.

The sequence of introducing the reagents is important in the context of the present invention. In fact, the reaction cannot be accomplished if the sequence of introducing the reagents and especially the sequence of introducing the sulfur dioxide and the trifluoromethyl bromide are reversed.

Among the metals employed by the process of the present invention, it is preferable to use zinc.

Among polar aprotic solvents, it is preferable to use amides such as, in particular, formamide, dimethylformamide, N-methylpyrrolidone, dimethylacetamide, or solvents such as sulfolane. The use of dimethylformamide is particularly preferred.

Among alkali metal dithionites, sodium and potassium dithionite are preferred. The use of sodium dithionite is particularly preferred.

Iodine is added dissolved in any carboxylic or sulfonic acid which does not react with the reaction medium. The use of carboxylic or sulfonic acids containing 1 to 4 carbon atoms is preferred. These acids may be perfluorinated. The use of acetic acid is particularly preferred.

According to a first preferred method for implementing the invention, employing a metal and sulfur dioxide together with the trifluoromethyl bromide, a ratio of moles of trifluoromethyl bromide to gram-atoms of metal of at least 2:1 and a ratio of moles of sulfur dioxide to gram-atoms of metal preferably ranging from 1:1 to 3:1 are introduced into the reactor. Any excess trifluoromethyl bromide can be recycled.

The quantity of solvent employed is such that there is preferably from 0.25 to 1 gram-atoms of metal per liter of solvent.

A second preferred method of implementing the invention employs an alkali metal dithionite.

For both the first and second preferred methods, a base chosen from among alkali metal hydroxides, alkaline earth metal hydroxides and ammonia or a weakly acidic salt such as, for example, disodium phosphate, sodium metabisulfite, sodium hydrogen phosphate, sodium hydrogen sulfite and sodium borate, is preferably added. The addition of disodium phosphate is particularly preferred.

According to a preferred method for implementing the invention, the alkali metal dithionite is introduced into the reactor as a saturated solution in water or in formamide. It is also possible to introduce a part of the dithionite in the form of a solid and the other part dissolved in water in the form of a saturated suspension. It is preferable to remove any oxygen present in the reactor and to then introduce the gaseous perhalomethane.

It is preferable to carry out the first stage of the reaction at a temperature ranging from 45° to 85° C. and even more preferably from 65° to 75° C.

The reaction pressure employed in the first stage according to the process is preferably greater than 1 bar, which is an essential condition when the reaction is carried out with a gas which is only slightly soluble in the reaction solvent. A pressure ranging from 1 to 50 bar is preferred, although the upper limit is not an essential condition.

At the end of the first stage of reaction carried out according to either the first or second method of implementation, the suspension obtained is preferably filtered, the sulfur dioxide, if introduced, is removed and iodine in a carboxylic or sulfonic solvent, which may be perfluorinated, is then added.

Iodine is employed in at least a stoichiometric quantity, calculated relative to gram-atoms of metal or to moles of dithionite. The ratio of moles of iodine to gram-atoms of metal or moles of dithionite preferably ranges from 0.5:1 to 2:1. It is preferable to work at a temperature ranging from 100° to 140° C. in this second stage.

The role of the carboxylic or sulfonic acid is to solubilize the iodine and to maintain the pH of the reaction medium at a level not greater than 5. Thus, the acid will be introduced in a quantity which is required to achieve this pH.

The reactor is made of a material inert to the reaction, i.e., it must not be made of a material or metal which can react with sulfur dioxide. The use of a glass reactor is preferred.

During the second stage, when iodine is introduced into the carboxylic or sulfonic acid, trifluoromethyl iodide is evolved instantaneously and is recovered in a cold trap.

In the second stage of the invention, the reaction of iodine with the reaction product of the first stage of the invention is conducted for a time sufficient to obtain the desired trifluoromethyl iodide. Illustrative times for the reaction of both the first and second stages of the invention are set forth in the examples.

The invention will be described more completely using the following examples which must not be regarded as limiting the invention.

EXAMPLE 1

The following were placed in a thick glass flask:
6.5 g of zinc,
4 g of sodium hydroxide powder, and
100 ml of dimethylformamide.

The flask was placed in a Parr bomb. After creating a vacuum, the following was added:
10 g of sulfur dioxide.

The pressure was then increased to 3.7 bar by adding bromotrifluoromethane. The mixture was stirred for 2 hours. The flask was then opened, the solids were removed by filtration and the remaining sulfur dioxide was evacuated under vacuum. The following were then added:
50 ml of glacial acetic acid, and
15 g of iodine.

The mixture was then heated to 120° C. for 9 hours.

An evolution of gas occurred. The gases were recovered in a cold trap using solid carbon dioxide and then distilled to give:
6.3 g of trifluoromethyl iodide (b.p.: −22° C.);
Yield: 32%.

EXAMPLE 2

The following were placed in a thick glass flask:
10 g of sodium dithionite dihydrate,
8 g of sodium hydrogen phosphate,
15 ml of water, and
10 ml of dimethylformamide.

The flask was placed in a Parr bomb. After creating a vacuum within the flask, the temperature was set at 65° C.

The pressure was then increased to 3.7 bar by adding bromotrifluoromethane. The mixture was stirred for 2 hours. The flask was then opened, the solids were removed by filtration, the water was evaporated off under vacuum, the dimethylformamide was recovered and the crystals formed were rinsed with two × 10 ml of dimethylformamide. The following were then added:
50 ml of acetic acid containing dimethylformamide, and
15 g of iodine.

The mixture was then heated to 120° C. for 3 hours. An evolution of gas occurred. The gases were recovered in a cold trap using solid carbon dioxide and then distilled to give:
0.6 g of trifluoromethyl iodide;
Yield: 6%.

We claim:

1. A process for the preparation of trifluoromethyl iodide which comprises the steps of, in a first stage, introducing into a polar aprotic solvent either a metal selected from the group consisting of zinc, cadmium, aluminum and manganese, together with sulfur dioxide, or an alkali metal dithionite; thereafter adding thereto trifluoromethyl bromide at a pressure greater than one bar for a time sufficient to react; and, in a second stage, adding iodine dissolved in a carboxylic or sulfonic acid to the reaction product of the first stage and reacting for a time sufficient to obtain said trifluoromethyl iodide.

2. The process of claim 1, wherein said metal is zinc.

3. The process of claim 1, wherein said polar aprotic solvent is dimethylformamide.

4. The process of claim 1, wherein said alkali metal dithionite is sodium dithionite.

5. The process of claim 1, wherein said carboxylic acid is acetic acid.

6. The process of claim 1, wherein said carboxylic or sulfonic acid is perfluorinated.

7. The process of claim 1, wherein the ratio of moles of said trifluoromethyl bromide to gram-atoms of said metal is greater than or equal to 2:1.

8. The process of claim 1, wherein the ratio of moles of said sulfur dioxide to gram-atoms of said metal ranges from 1:1 to 3:1.

9. The process of claim 1, wherein 0.25 to 1 gram-atoms of said metal are employed per liter of said solvent.

10. The process of claim 1, wherein either said dithionite or said combination of metal and sulfur dioxide is employed in the presence of a base or a weakly acidic salt.

11. The process of claim 10, wherein said weakly acidic salt is disodium phosphate.

12. The process of claim 1, wherein said dithionite is introduced as a saturated solution in water or in formamide.

13. The process of claim 1, wherein the ratio of moles of said iodine to gram-atoms of said metal or to moles of said dithionite ranges from 0.5:1 to 2:1.

14. The process of claim 1, wherein said reaction pressure employed in said first stage ranges from 1 to 50 bar.

15. The process of claim 1, wherein the reaction temperature employed in said first stage ranges from 45° to 85° C.

16. The process of claim 15, wherein said reaction temperature employed in said first stage ranges from 65° to 75° C.

17. The process of claim 1, wherein the temperature employed in said second stage ranges from 100° to 140° C.

18. The process of claim 1, wherein solids formed in said first stage are removed by filtation prior to said second stage.

* * * * *

UNITED STATES PATENT AND TRADEMARK OFFICE
CERTIFICATE OF CORRECTION

PATENT NO. : 4,794,200

DATED : December 27, 1988

INVENTOR(S) : Marc TORDEUX et al.

It is certified that error appears in the above-identified patent and that said Letters Patent is hereby corrected as shown below:

IN THE ABSTRACT:

In line 5 of the Abstract, change "zinc, sulfur" to --(a) zinc, sulfur--.

IN THE CLAIMS:

Claim 18, column 6, line 11, change "filtation" to --filtration--.

Signed and Sealed this

First Day of August, 1989

Attest:

DONALD J. QUIGG

Attesting Officer

Commissioner of Patents and Trademarks